United States Patent
McClure et al.

[11] Patent Number: 6,161,043
[45] Date of Patent: Dec. 12, 2000

[54] IMPLANTABLE CARDIAC DEVICE HAVING EVENT RECORDING CAPABILITY WITH COMPRESSION

[75] Inventors: Kelly H. McClure, Simi Valley; Gabriel Mouchawar, Newhall; Timothy J. Starkweather; James D. Causey, III, both of Simi Valley, all of Calif.

[73] Assignee: Pacesetter, Inc., Sylmar, Calif.

[21] Appl. No.: 09/255,140

[22] Filed: Feb. 22, 1999

[51] Int. Cl.⁷ .................................................. A01B 5/0452
[52] U.S. Cl. .................................................................. 607/27
[58] Field of Search ........................... 607/27, 32, 9

[56] References Cited

U.S. PATENT DOCUMENTS

| | | | |
|---|---|---|---|
| 4,449,536 | 5/1984 | Weaver | 128/696 |
| 4,567,883 | 2/1986 | Langer | 128/696 |
| 4,633,884 | 1/1987 | Imai | 128/696 |
| 4,716,903 | 1/1988 | Hansen et al. | 128/419 |
| 4,802,222 | 1/1989 | Weaver | 381/35 |
| 4,882,754 | 11/1989 | Weaver et al. | 381/35 |
| 4,947,858 | 8/1990 | Smith | 128/696 |
| 5,215,098 | 6/1993 | Steinhaus et al. | 128/702 |
| 5,217,021 | 6/1993 | Steinhaus et al. | 128/702 |
| 5,263,486 | 11/1993 | Jeffreys | 128/696 |

*Primary Examiner*—Scott M. Getzow

[57] ABSTRACT

An implantable cardiac device is disclosed having a converter that provides a digital electrocardiogram signal to a controller which is stored in memory or transmitted via the telemetry circuit in an improved compressed fashion. The improved compression scheme comprises sampling the electrogram signal, transmitting the starting value in an uncompressed format followed by a plurality of delta signals in a compressed format. The delta signals may be determined by subtracting successive signals or by subtracting a predicted value from the current value. In either case, the delta signal is then transmitted in a truncated number of bits, e.g., 2 or 4 bits. When the delta signal is too large to be represented in the compressed number of bits, the controller then provides an indicator signal followed by the delta signal in the uncompressed format. In addition, whenever successive delta signals are below a minimum threshold (e.g., zero), they may be compressed into a count.

35 Claims, 8 Drawing Sheets

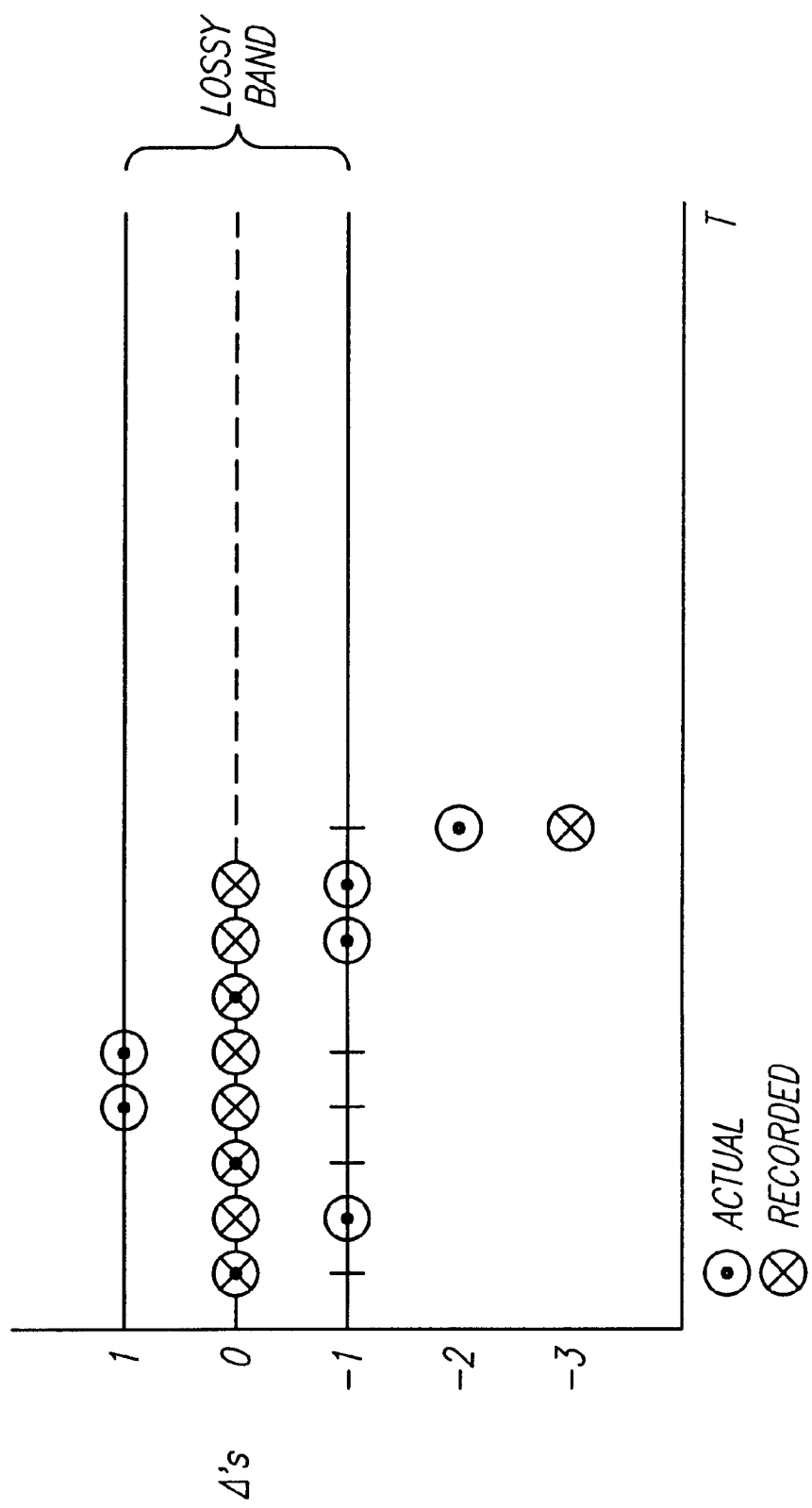

IMPLANTABLE CARDIAC DEVICE HAVING EVENT RECORDING CAPABILITY WITH COMPRESSION

FIELD OF THE INVENTION

The present invention relates to implantable cardiac devices and, in particular, implantable cardiac devices having event recording capability wherein the electrogram and event data is stored in a compressed format for subsequent downloading to an external device.

BACKGROUND OF THE INVENTION

Implantable cardiac devices include devices such as pacemakers and implantable cardioverter-defibrillators (ICD's). These are devices which are configured to be implanted within the body of the patient and have leads that are adapted to be positioned adjacent the walls of the heart that can provide therapeutic electric electrical stimuli to the heart. Over time, implantable cardiac devices have become more sophisticated. The current generation of implantable cardiac devices are capable of sensing the occurrence of a particular arrhythmia and then providing an appropriately configured therapeutic electrical shock or stimulus.

For example, an implantable cardioverter-defibrillator will be able to sense the occurrence of a ventricular fibrillation episode and provide a defibrillation shock to the heart to restore normal rhythm. Similarly, current generation pacemakers are capable of providing pacing pulses to the heart upon detecting an absence of appropriate intrinsic activity of the heart.

These implantable cardiac devices are also equipped with sensing circuits that provide an indication as to the intrinsic activity of the heart. These sensing circuits provide the input which allows the implantable cardiac device to selectively apply the appropriately configured therapeutic electrical stimuli. Typically, these implantable cardiac devices can continuously monitor the heart and store a plurality of diagnostic signals contemporaneously with therapy. The recorded data can then be subsequently downloaded, via a telemetry system, to an external device, thereby allowing a physician to observe the event which triggered the therapeutic action at a later time.

Being able to review a record of the heart's activity during a cardiac event necessitating the application of a stimulation therapy is a very valuable diagnostic tool for the physician. For example, repeated occurrence of a particular cardiac event may be indicative of an additional problem suffered by the patient that would necessitate additional treatment.

It allows configuration of the device to give the best therapy, and provides information about the progress of the disease that can guide prescription of the treatment.

However, one difficulty with current implantable cardiac devices is that the recording capability is often limited. For example, a device that has 128 Kbytes of memory and samples the electrogram signal with 8-bit resolution at a rate of 256 samples/second can store only approximately eight minutes of electrograms. As patients may visit their physicians only periodically, eight minutes of recording time may be insufficient to capture an electrogram of a significant number of the episodes that occurred during the interval between the patient's visits to the doctor.

Hence, certain events are either not recorded or, if they are recorded, they are overwritten by more recent events. This loss of data can impede the ability of the physician assess the patient's condition.

Hence, there is a need to increase the memory capacity of the implantable cardiac device so that more data can be recorded. However, the design constraints of implantable cardiac devices impose limits on the amount of memory which can be included in the device. In particular, the controller for implantable cardiac devices are generally very small in size and space for memory is generally at a premium. Further, implantable cardiac devices are also battery operated and the addition of processing circuitry to increase memory capability may result in a decrease in the active life of the implantable cardiac device. Battery depletion will necessitate replacement, which requires an invasive surgical procedure. Therefore, a decrease in the active life of the implantable cardiac devices to improve memory capabilities is generally undesirable.

Data compression is one way of increasing the amount of data that can be stored in a memory, without increasing the size of the memory. Compression generally means storing the data in such a manner that it requires less memory space. Subsequently, when the stored data is downloaded, the compressed data can then be reconstructed into its original form.

There are generally two types of compression schemes, lossy and lossless. Lossy compression schemes yield a higher compression ratio than lossless schemes, at a cost of some loss in data following reconstruction. A lossy compression scheme is a compression scheme which stores the original data in such a fashion that when reconstructed, the reconstruction data is not an exact replication of the original data. Generally, lossy schemes determine that some portion of the data is less important and will therefore not store as precisely these portions of the data.

Lossless schemes compress the data in a manner which allow the data to be reconstructed such that the reconstructed data is the same as the original data.

While compression schemes are commonly used in applications such as digital communications, they have generally not been used in implantable cardiac devices. One reason for this is that compression schemes often require significant processing. The processing requirements to implement most compression schemes generally have a negative impact on the battery life of an implantable cardiac device. Further, prior art efforts to implement compression schemes to compress electrograms in implantable cardiac devices have often necessitated the inclusion of additional components into the implantable cardiac device. These additional components take up valuable space in the implantable device and consume additional power from the batteries.

One example of such a prior art application of compression schemes to implantable cardiac devices is provided by U.S. Pat. No. 4,716,903 to Hanson et al. which discloses a pacemaker memory that has a compression circuit which allows for an electrogram signal to be compressed. In particular, U.S. Pat. No. 4,716,903 compresses a digital conversion of an electrogram signal by recording the positive or negative changes in the signal and also recording the elapsed time between each change. This compression scheme requires the addition of registers, adders and a clock to implement the compression scheme. Each of these components take up additional space in the limited space environment of the pacemaker controller. Further, each of these additional components must be powered by the battery and therefore diminish the active life of the battery and of the implantable cardiac device.

Hence, there is a need for an implantable cardiac device which has enhanced recording capability that does not require a significant number of additional components or result in significant consumption of battery power. To this end, there is a need for an implantable cardiac device which has the ability to compress event data in a manner that is efficient in terms of power consumption and also in terms of consumption of limited space within the control unit of the implantable device.

SUMMARY OF THE INVENTION

The aforementioned needs are satisfied by the present invention which is comprised of an implantable cardiac device that is adapted so as to receive and store data (e.g. cardiac signals) in a compressed form which draws very low power and utilizes very little memory.

A first feature of the present invention is that the compressed signal comprises an initial value, corresponding to the starting amplitude of the cardiac signal, followed by a plurality of delta values corresponding to subsequent changes from the previous value.

To prevent any loss in the signal, the present invention transmits large delta values in an uncompressed format using a first set of bits (e.g., 8 bits) and transmits small delta values in a compressed format using a second set of bits (e.g., 2 bits).

To distinguish between the two types of delta values, an indicator flag is transmitted prior to each uncompressed delta value. More specifically, whenever the signal exceeds a prescribed threshold, thereby indicating a large signal change, an indicator flag is transmitted to indicate that the next set of bits, in an uncompressed format, contain the new delta value.

The implantable cardiac device typically has at least one lead adapted to be positioned in contact with cardiac tissue and includes a pulse generator to deliver a therapeutic electrical stimulus to the heart, a sensing circuit which senses the activity of the heart, and a controller which receives the sensed cardiac signal.

In one embodiment of the present invention, the implantable cardiac device incorporates a controller and memory wherein the controller receives a heart event signal such as an electrogram signal. The controller converts the analog electrogram data into a digital signal of a first set of bits, and records, in the memory, the electrogram signal following the initiation of a cardiac event in a compressed manner.

In another embodiment, compression scheme of the invention may be adapted to transmit real-time electrograms directly to an external programmer through the telemetry system. Advantageously, the present invention significantly minimizes the bandwidth required for downloading this information.

In particular, in this embodiment, a majority of the changes in the digital signal from the preceding sample are stored in 2-bits of the memory. With an appropriate sampling rate, a substantial number of the changes between two successive digital signals or samples are comprised of no change, a 1-bit change in the positive direction, or a 1-bit change in the negative direction.

Hence, the controller is capable of storing the substantial number of changes from the initial value in one of three 2-bit combinations. In the event that the change in the digital value of the electrogram signal is greater than a single bit, the fourth 2-bit combination can be used as an indicator bit to indicate that a subsequent number of bits define the change in value. In this way, compression of the electrogram signal can be achieved without the requirement of additional components and further without the significant additional processing. This compression is lossless.

In another embodiment of the invention, the controller that receives the cardiac signal, samples the signal and digitizes each of the samples into a plurality of bits, such as a byte (8 bits). At the beginning of the cardiac event, the initial value is recorded in the memory. Subsequently, changes in the initial value are recorded using a limited number of bits. Within a nibble (e.g., 4 bits) values from −8 to +7 can be stored. However, one of the values (−8) must be used as an indicator of when the data exceeds the 4-bit range. In such a case, the following byte after the indicator −8 contains the data. Also, the value 7 is used to count the consecutive values of zero. The compression is further enhanced by determining the number of sequential samples in which no change has occurred and storing a signal representative of this number.

In another embodiment of the present invention, the compression schemes implemented by the controller can be adapted so as to be lossy. In particular, the controller can be configured so that small changes from a baseline value will be recorded as the baseline value. It will be appreciated that a standard electrogram signal can have relatively flat periods where the signal has only small changes. Hence, the compression ratio of the data of this type can be increased by assuming that changes in the incoming heart event signal that are smaller than a threshold value correspond to relatively linear portions of the heart event signal. Hence, this portion of the signal can be stored in a more compressed fashion without a significant loss of important information. In one embodiment, the controller is configured to store all changes that are lower than the threshold as no change and then only store the change in value when the sum of these changes has increased beyond the threshold level. In this fashion, the compression can be enhanced as the changes below the threshold value can all be stored as a number of sequential samples in which there was no change.

The embodiments of the present invention, therefore provide a controller that is capable of storing heart event data that is indicative of the function of the heart during a cardiac event in either a lossy or lossless fashion. The compression schemes implemented by the implantable cardiac device of the present invention function by simply storing the changes in value from one sample to another sample. When the change cannot be accounted for by the limited number of bits, a limited number of bits is then used as an indicator to indicate that the next set of bits defines the new change. Using these techniques, compression ratios on the order of two or three to one can be achieved. Hence, two to three times the amount of information can be stored in the memory of an implantable cardiac device for subsequent transmission to an external device.

These and other advantages of the present invention will become more fully apparent from the following description taken in conjunction with the accompanying drawings.

BRIEF DESCRIPTION OF THE DRAWINGS

FIG. 7 is an exemplary set of data points illustrating how the controller, implementing the compression scheme illustrated in FIGS. 5A and 5B, would convert an exemplary number of data points.

DETAILED DESCRIPTION OF THE PREFERRED EMBODIMENTS

Figure 1:
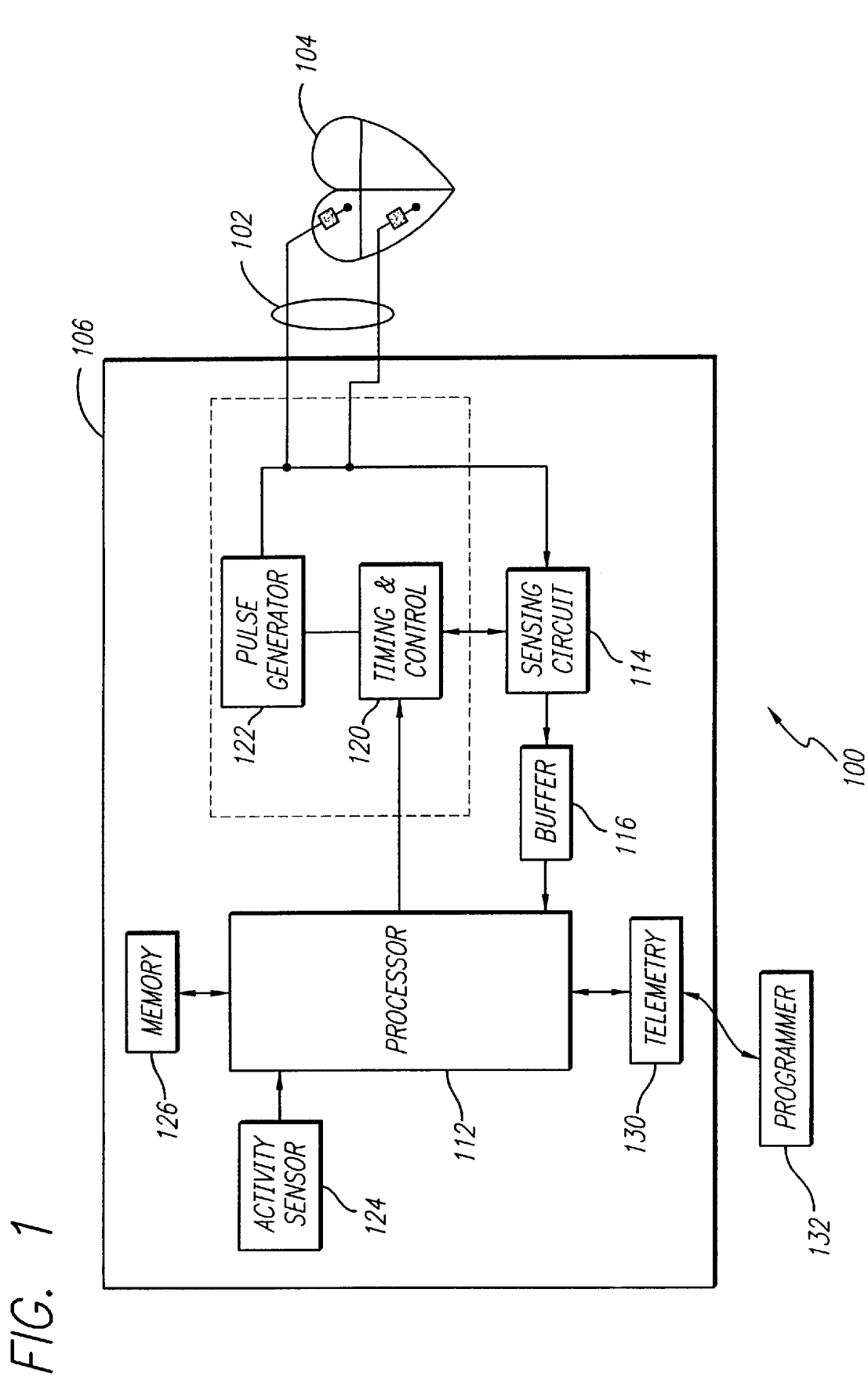
FIG. 1 is a functional block diagram of one embodiment of an implantable cardiac device.

Reference will now be made to the drawings wherein like numerals refer to like parts throughout. FIG. 1 is a block diagram which illustrates an exemplary implantable cardiac device 100 of the preferred embodiment. The implantable cardiac device 100 includes one or more leads 102 that are adapted to be positioned adjacent walls of the heart and preferably within chambers of the heart 104, although this invention can be used and is claimed for data from any biological sensor. The one or more leads 102 are attached to a controller 106 so that the controller 106 can induce the leads 102 to provide therapeutic electrical stimuli to the heart 104 in a well known fashion. Specifically, a processor 112 can induce the leads 102 to deliver therapeutic electrical stimuli, such as pacing pulses or defibrillation pulses, by triggering a timing and control circuitry 120 and a pulse generator 122 to develop the appropriate therapeutic waveform which is then provided to the leads 102. The operation of the implantable cardiac device 100 in delivering therapeutic pulses is substantially identical to the operation of prior art implantable cardiac devices.

At least one of the leads 102 functions to deliver cardiac signals to a processor 112 via a sensing circuit 114 and a buffer 116. The signal in the preferred embodiment is an intracardiac electrogram (EG) signal. The sensing circuit 114 samples the incoming electrogram signal at a fixed sampling rate, e.g., 128 Hz or 256 Hz, and then outputs a corresponding digital output in the manner that is described in more detail with respect to FIG. 2. The digital output is then buffered in the buffer 116 and is provided to the processor 112 so that the processor 112 can determine whether to provide therapeutic electrical stimuli to the heart 104. The processor 112 may also receive signals from an activity sensor 124 or any of a number of well known sensors which provide further information to the processor 112 to facilitate the processor 112 in delivery therapeutic electrical stimuli to the heart 104 via the leads 102.

The processor 112 also has an associated memory 126 where information provided by the sensing circuit 114 can be stored. Similarly, the processor 112 is also associated with a telemetry circuit 130 which allows for communication between an external programmer 132 and the controller 106.

The implantable cardiac device 100 can be configured as either a pacemaker, or as an implantable cardioverter-defibrillator (ICD), or both. In this respect, the controller 106 is adapted to sense the function of the heart and in conjunction with other sensor signals provided by additional sensors 124, deliver appropriate therapeutic stimuli to the heart 104 via the leads 102. The therapeutic stimuli can either be a pacing pulse or a defibrillation pulse depending upon the configuration of the implantable cardiac device 100. Advantageously, the controller 106 is configured so that the electrogram data provided by the sensing circuit 114 can be stored in the memory 126 in a compressed fashion. The compression schemes implemented by the controller 106 are described in greater detail in reference to FIGS. 3, 5A, 5B, 7 and 8 below.

Figure 2:
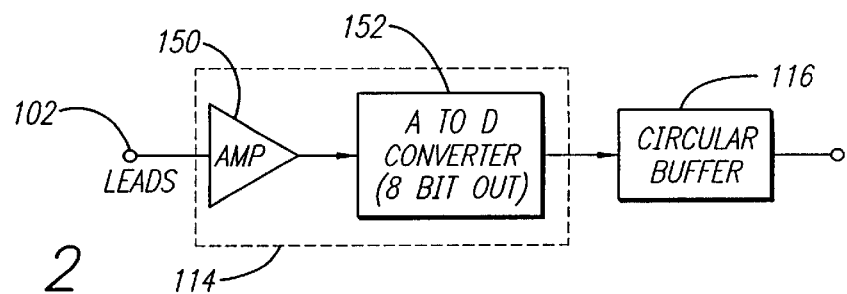
FIG. 2 is a functional block diagram of circuitry within the implantable cardiac device of FIG. 1 that converts an analog signal such as an electrogram signal into a digital value which are subsequently stored in a buffer.

FIG. 2 illustrates a portion of the controller 106 in greater detail. In particular, in this embodiment of the implantable cardiac device 100, the sensing circuit 114 includes an amplifier 150 that receives the electrogram signal from the leads 102. The amplified signal is then provided to an A/D converter 152 which provides an eight-bit digital output signal. Preferably, the digital output from the A/D converter 152 is provided at a fixed sampling rate, e.g., either 128 Hz or 256 Hz, to the buffer 116. The buffer 116 is preferably a circular buffer of the type known in the art wherein a fixed number of digital signals are stored within the buffer and the oldest buffered signal is replaced by the newest signal provided by the A/D converter 152.

Alternately, a delta converter may be employed instead of the A/D converter, wherein one of skill in the art could readily configure the delta converter, with a summer circuit, to calculate the starting value rather than simply delta values.

In this fashion, the buffer 116 is capable of providing information to the processor 112 of the function of the heart during a previous interval of time. It will be understood that the processor 112 is programmed to review the data stored within the buffer 116 and then determine if an event has occurred which requires the application of a therapeutic electrical stimuli to the heart 104 via the leads 102. Other criteria such as morphology or intrinsic rate may be used to determined if a cardiac event has occurred.

For example, if the implantable cardiac device 100 is configured to be an implantable cardioverter-defibrillator, the controller 112 is programmed to recognized from the electrogram signal the occurrence of ventricular fibrillation. This will result in the programmer 112 inducing the timing and control circuit 120 and the pulse generator 122 to provide a therapeutic electrical stimuli to the ventricles of the heart 104 via the leads 102 that is configured to halt the ventricular fibrillation and restore the heart to a normal sinus rhythm.

As an alternative example, if the implantable cardiac device 100 is configured to be a pacemaker, the processor 110 may be configured to recognize from the electrogram signal that the ventricle has failed to depolarize within a set interval and can then apply an appropriately configured pacing pulse to the ventricle of the heart 104 via the leads 102. In this fashion, the processor 112 operates in the manner that is similar to the manner of operation of implantable cardiac devices of the prior art.

Hence, in this embodiment, the processor 112 is receiving an eight-bit digital signal at a fixed frequency that is indicative of the function of the heart. As is known in the art, the buffered signals and subsequently received signals from the sensor 110 can be stored in the memory 126 upon the processor 112 determining that a cardiac event necessitating the application of therapeutic electrical stimuli has occurred. Advantageously, the processor 112 of the this embodiment is adapted to store the electrogram data in a compressed fashion in the memory 126.

Figure 3:
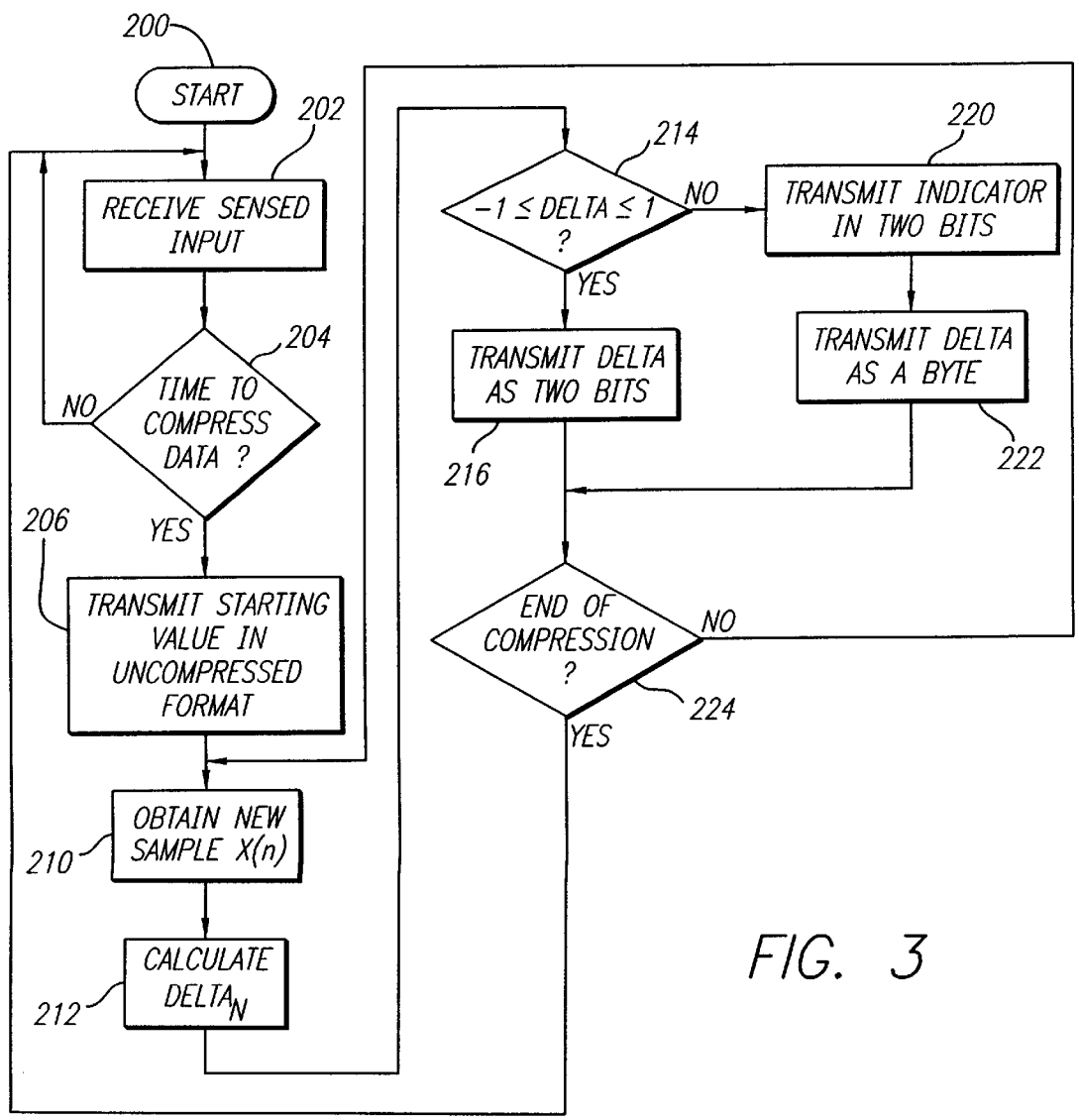
FIG. 3 is an exemplary flow chart illustrating the operation of a controller of the implantable electrical device as a first lossless compression scheme is implemented on an electrogram signal.

FIG. 3 is a flow chart which illustrates one exemplary compression scheme implemented by the processor 112 in storing the electrogram data from the sensing circuit 114 in a compressed fashion in the memory 126. In particular, the processor 112 starts (Block 200) by initially receiving input from the sensing circuit 114 (Block 202). The processor 112 determines (Block 204) whether it is time to compress the data (i.e., whether a cardiac event or a real-time telemetry request has occurred).

In a first embodiment, the processor 112 determines (Block 204) if it is time to compress the data based on whether a request has been made for real-time electrograms. If yes, then the processor will compress the data and transfer it to the telemetry circuit 130.

In a second embodiment, the processor 112 evaluates the incoming electrogram and determines whether an arrhythmic event is occurring (such as ventricular tachycardia, ventricular fibrillation or a failure of to capture the heart, has occurred) in order to ascertain whether therapeutic electrical stimuli should be provided by the leads 102. In the event that the processor 112 determines that an event necessitating therapeutic action has occurred (Block 204), the processor 112 initiates a process whereby a therapeutic electrical stimuli is provided to the heart in a known manner and also initiates a recording function whereby electrogram data is recorded in the memory 126 in a compressed fashion.

Since the present invention may either "store" the initial value and the delta values to memory, "send" them directly to the telemetry circuit, or perform a combination of storing and sending, the encoding of the compressed data will hereinafter be referred to as "transmitting" the data to cover all conditions.

The processor 112 obtains (Block 206) an initial value and transmits this initial value in an uncompressed format (e.g., as an eight-bit digital value) corresponding to the actual starting amplitude or voltage level of the electrogram provided by the sensing circuit 114. Subsequent data points (as discussed below) that are compressed by the processor 112 are the changes between successive samples of the electrogram signal, and are hereinafter referred to as the delta values.

Hence, once the processor 112 has transmitted the initial starting value (Block 206), the processor 112 then obtains a new sample (Block 210) and calculates (Block 212) the next delta value, for example, according to the following formula:

$$DELTA_n = x(n) - x(n-1).$$

Hence, for each new digital sample, the processor 112 is subtracting the newest eight-bit digital value from the buffer 116 from a preselected value, which, in this embodiment, is comprised of the previously received eight-bit digital sample received from the buffer 116. Alternately, any type of subtractor circuit could be used in lieu of the processor determining the difference between x(n) and x(n-1).

Figure 5A:
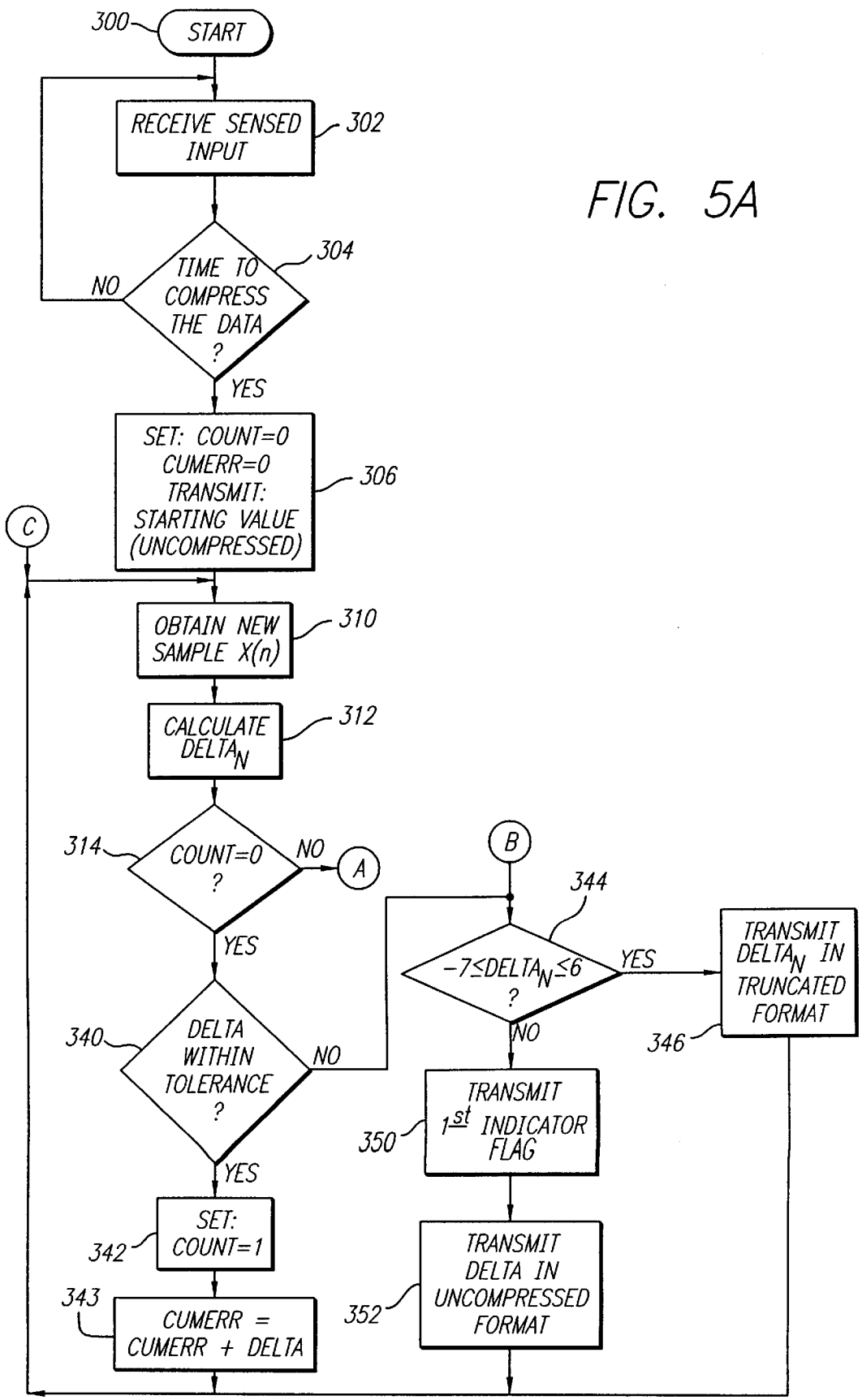
FIGS. 5A and 5B comprise an exemplary flow chart illustrating a second lossy compression scheme convert an electrogram signal into a compressed format.
Figure 5B:
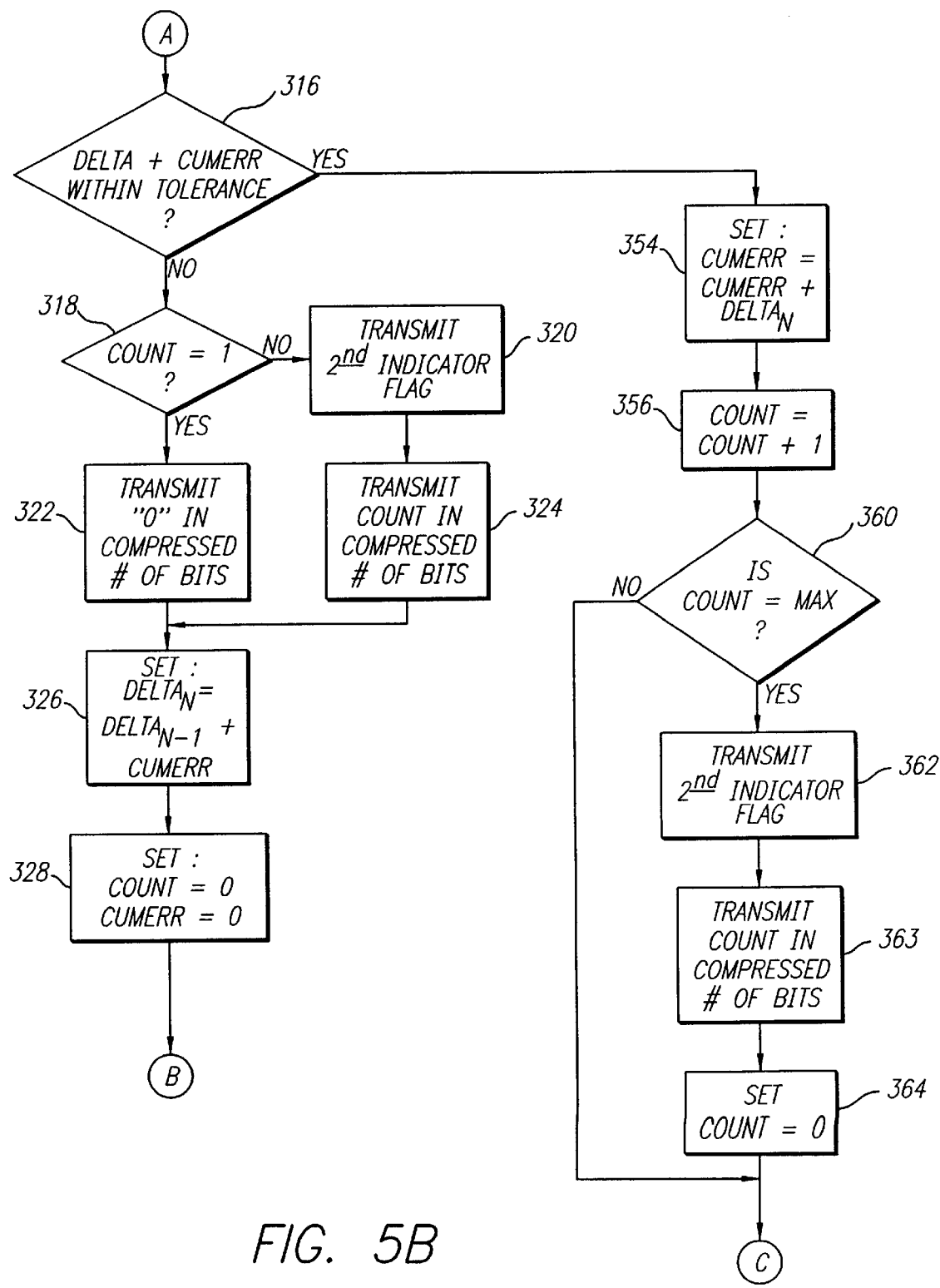

It will be appreciated that since the A/D converter 152 in this embodiment is providing an eight-bit binary output, the delta value, $DELTA_n$, will also be comprised of an eight-bit binary number. However, as will be described in greater detail below, the eight-bit delta value can, in the majority of cases, be truncated (without loss of information) to a 4-bit value (as illustrated in FIGS. 5A and 5B) or, in the preferred embodiment, to a 2-bit delta value (as illustrated in FIG. 3).

Once the processor 112 has determined the delta value, $DELTA_n$, the processor 112 then determines (Block 214) whether the delta value, $DELTA_n$, is within a first prescribed threshold. In the preferred embodiment, shown in FIG. 3, a 2-bit delta value is employed with the first prescribed threshold being a single bit positive change or a single bit negative change. However, it is within the spirit of the invention that the first prescribed threshold could be set appropriately for a 4-bit delta value, and one of skill in the art could readily modify the method shown in FIG. 3 to accommodate a 4-bit delta value and a corresponding first threshold.

The Applicant has determined that using either a 128 or a 256 Hz sampling rate for most cardiac electrogram data, the majority of the delta values, $DELTA_n$, will be a single bit positive change, a single bit negative change or no change.

In particular, using data extracted from the Ann Arbor Electrogram Library, Volume I, comprising a data set containing ventricular electrograms for 52 patients with a mix of normal sinus and arrhythmia corresponding to what would be expected with patients with patients with implantable cardiac devices, the Applicant converted the data in to approximately 900,000 delta samples assuming a 256 Hz sampling rate. Of the 900,000 delta samples, approximately 450,000 of the delta values are equal to zero. Similarly, there were 750,000 delta values where the difference in amplitude between successive samples as calculated by above-identified equation was equal to no change, a single bit positive change, or a single bit negative change. Therefore, the Applicant has determined that approximately 80% of the delta values $DELTA_n$ as calculated according to above-identified equation using eight-bit electrogram data provided at an appropriate sampling rate (e.g., either a 128 or 256 Hz) can be stored in two's complement notation as one of three 2-bit delta values: 00 corresponding to no change, 01 corresponding to a single bit positive change, or 10 corresponding to a single bit negative change.

Consequently, if the processor 112 determines (Block 214) whether the delta value, $DELTA_n$, is between −1 and 1, then the processor 112 (Block 216) converts the delta value calculated (Block 212) into a 2-bit value according to Table 1 and stores this 2-bit value in the memory 126.

TABLE I

| Delta Values, $DELTA_n$: | −1, 0, +1 |
|---|---|
| Stored Bit Representation: | 01, 00, 10 |

It will be appreciated for each new eight-bit sample that is provided by the A/D converter 152, only a 2-bit delta value, $DELTA_n$, has to be transmitted in the majority of cases. Hence, for the majority of the sampled electrogram data points, there is a 4:1 compression ratio.

However, not all the delta values, $DELTA_n$, will be a 1, −1, or 0. When the electrogram signal is changing very rapidly, there may be very significant changes in the amplitude of the electrogram signal. Consequently, the delta value, $DELTA_n$, calculated (in Block 212) may be larger than 1, 0 or −1.

Hence, in the event that the processor 112 determines (Block 214) that the delta value, $DELTA_n$, is not between −1 and 1, then the processor 112 transmits an indicator (Block 220). The indicator indicates that a preselected number of following bits stored in the memory 126 are indicative of the next delta value (Block 222). In this embodiment, an indicator of "11" is used to indicate that the following eight-bit (byte) contains the next delta value. Hence, the majority of the delta values, DELTA$_n$, can be transmitted as 2-bit values, however a minority of the delta values, DELTA$_n$, must be transmitted in an expanded form. The overall impact of using the compression scheme is to obtain compression ratios that are on the order of 2 or 3 to 1.

In particular, Table II illustrates selected compression ratios calculated for data sets originating from the Ann Arbor Electrogram Library, Volume I, that were compressed according to the above-described compression scheme.

TABLE II

| Data Set Permutation | Compression Ratio |
| --- | --- |
| Raw data with nominal gain | 2.97 |
| Filtered data with nominal gain | 3.22 |
| Filtered data with high gain | 2.10 |

As shown in Table II, the compression ratio is dependent upon how the incoming electrogram signal is filtered and also how much gain is applied to the signal. An increase in gain will result in more delta values that are greater than −1, 0 or 1 and therefore decrease the compression ratio. Similarly, by filtering noise out of the incoming electrogram circuit in a well known manner can enhance the compression ratio as there are fewer changes in the delta value that are the result of noise.

The processor 112 repeats this process for each of the incoming samples provided by the A/D converter 152 until it determines (Block 224) that the request for data compression has ended (i.e., either the arrhythmic event has ended or the real-time telemetry request has been terminated or timed-out).

In this way, each time an event trigger occurs, the data can be stored in the memory 126 in a compressed fashion such that significantly less of the memory 126 is used to store the data thereby allowing the memory 126 to accommodate more data.

Likewise, each time a real-time telemetry request occurs, the data can be transmitted to the telemetry circuit 130 in a compressed fashion such that it takes significantly less bandwidth to transfer the data.

Figure 4:
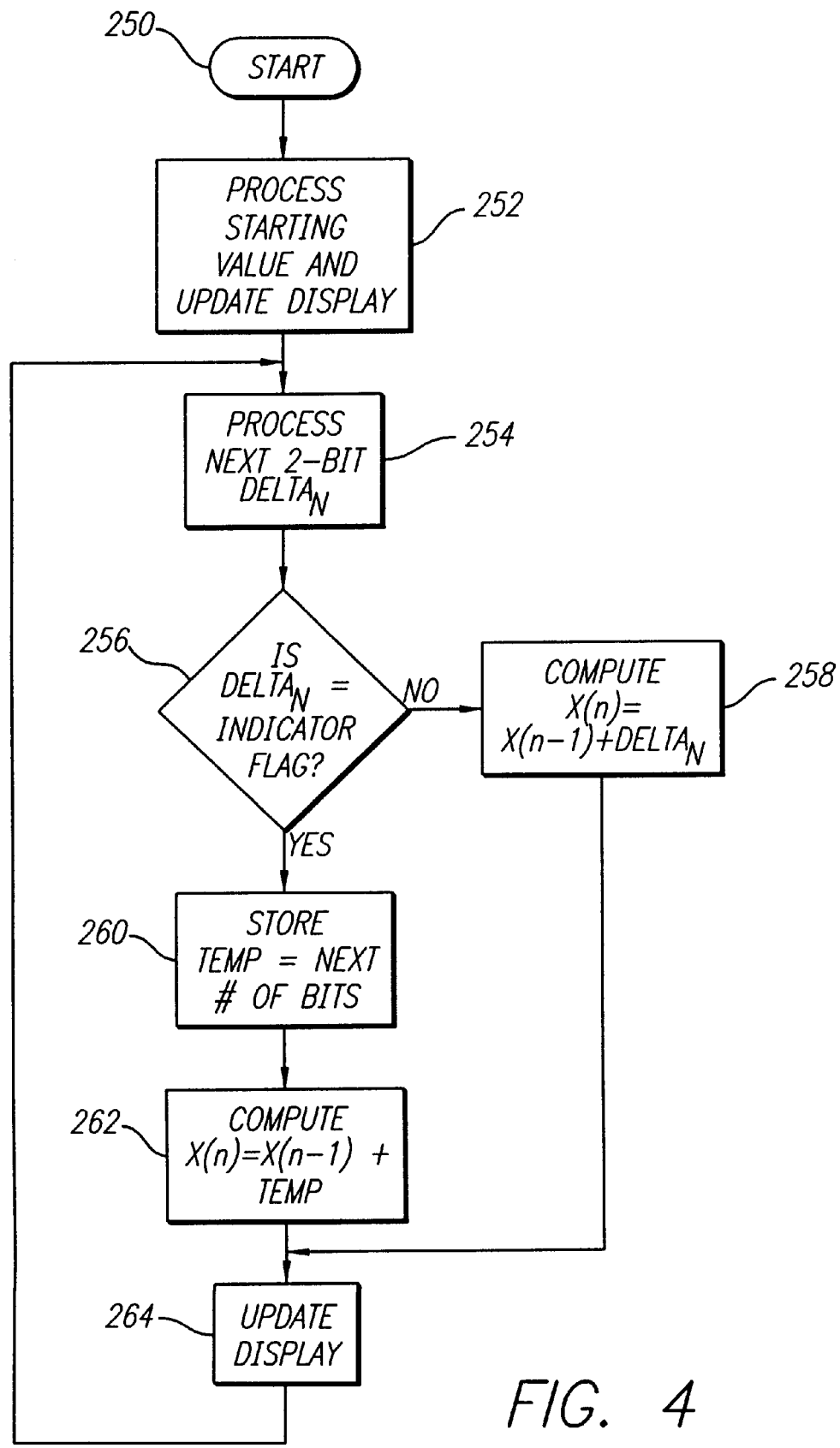
FIG. 4 is an exemplary flow chart illustrating the operation of an external programmer as data, compressed in accordance with the lossless compression scheme of FIG. 3, is reconstructed after this data has been retrieved from the memory of the implantable cardiac device.

FIG. 4 is a flow chart which illustrates the operation of the external programmer 132 (FIG. 1) as it reconstructs the compressed electrogram signal in the manner described above in reference to FIG. 3. The external programmer 132 can be comprised of any of a number of well known external programmers which includes a processor and a display. The external programmer 132 can be manipulated by a treating physician so as to trigger the processor 112 to download the compressed electrogram signal (either stored data from the memory 126 or real-time data directly from the implanted device) to the external programmer 132 via the telemetry circuit 130. The external programmer 132 in this embodiment is further configured so as to be able to reconstruct the electrogram signal from the compressed data corresponding to the particular event.

The programmer 132 operates in the following manner. Initially, from a start condition (Block 250), the programmer 132 processes the starting value (Block 252) and then updates the display. The starting value in this embodiment is the eight-bit digital signal which was representative of the actual amplitude of the electrogram signal. The electrogram may be the result of an event triggered event, (such as the electrogram stored in the memory 126 in Block 206 of FIG. 3) or a real-time electrogram initiated by the physician.

Subsequently, the programmer 132 processes (Block 254) the next two bits of compressed data which correspond to the compressed DELTA$_n$ value. As discussed above, the two bits of data are representative of the change between successive samples received by the processor 112. In particular, the two bits of data are either going to be representative of a 1-bit change, either positive or negative, in amplitude between successive samples, no change in the amplitude between successive samples, or will comprise an indicator indicating that the change between successive samples is greater than a 1-bit change in either direction.

Hence, the programmer 132 determines (Block 256) whether the next two bits are an indicator flag. As described above, in this embodiment, the indicator flag is "11".

In the event that the next two bits were not the indicator flag, then the amplitude of the next sample x(n) that was processed by the processor 112 during compression of this data is computed to be equal to the previous value x(n−1) plus the stored delta value DELTA$_n$ as determined by the programmer 132 (Block 258).

$$x(n)=x(n-1)+\text{DELTA}_n.$$

The amplitude value (x$_n$) can then be used to update the display of the electrogram signal by the programmer 132 (Block 264) in a well known manner.

In the event that the programmer 132 determines that the delta value, DELTA$_n$, is the indicator flag ("yes" at Block 256), then the programmer 132 stores the next preselected number of bits (e.g., 8) into a temporary variable, TEMP (Block 260). In this embodiment, when the stored delta value, DELTA$_n$, is equal to the indicator flag (e.g., "11"), then the TEMP variable will be set to the next preselected number of bits (e.g., 8 bits). This preselected number of bits is representative of the amplitude of the uncompressed delta value, DELTA$_n$, that was determined by the processor 112 during the compression function described above in reference to Block 222 in FIG. 3.

The external programmer then calculates the amplitude of the electrogram signal (Block 262) according to the following formula:

$$x(n)=x(n-1)+\text{TEMP}.$$

This amplitude value is then used to update the display (Block 264) in a well known manner.

Hence, the programmer 132 is preferably configured to be able to obtain an initial starting value for x(n), which provides a starting amplitude value of the electrogram signal. Subsequently, the delta values, DELTA$_n$, corresponding to each of the samples obtained by the processor 112 from the A/D converter 152 in the manner described above in conjunction with FIG. 3 are then sequentially added to calculate the sequential amplitude values of the electrogram signal. In this way, the electrogram signal can be completely reproduced from the compressed data.

It will be appreciated that the compression scheme described above with reference to FIGS. 3 and 4 is a substantially lossless compression scheme. Specifically, the electrogram signal that is reproduced by the programmer 130 is substantially equal to the digital electrogram signal that is provided by sensing circuit 114. In particular, the digital signal that is emanating from the A/D converter 152 and the sensing circuit 114 is fully reproduced upon reconstruction of the signal by the programmer 132.

It will be appreciated that the compression scheme described in reference to FIGS. 3 and 4, had certain advantages over compression schemes of the prior art used in conjunction with implantable cardiac devices. In particular, this embodiment of the implantable cardiac device is capable of compressing data and achieving compression ratios of approximately 3:1 without adding additional components to the controller 104. Further, the processor 112 only has to perform digital subtraction and then determine whether the resulting value is either no change, a 1-bit change in either direction, or greater than a 1-bit change.

Subsequently, the processor 112 transmits either the resulting 2-bit delta value or an indicator indicating that the actual resulting value in the next, e.g., 8 bits is to be used in reconstructing the x(n). This type of processing by the processor 112 does not require a significantly more powerful processor which would require more power from the battery. Hence, this embodiment of an implantable cardiac device implementing this compression scheme allows for more data of cardiac events to be compressed without a significant impact on the longevity of the implantable cardiac device and also without requiring the significant addition of components to implement the compression scheme.

In another embodiment, the implantable cardiac device 100 incorporates a lossy compression scheme. As is understood in the art, some compression schemes compress data in such a manner that when the compressed data is reconstructed, the reconstructed signal is not identical to the initial signal that was received by the processor. However, the lossy compression scheme that is implemented in this embodiment, is adapted so that the loss does not affect the rapidly changing portions of the electrogram. Instead, the loss occurs when the signal is slowly changing near its baseline. FIGS. 5A and 5B are a flow chart which illustrate the operation of the processor 112 in this embodiment as it implements this lossy compression scheme.

In particular, after the processor 112 starts (Block 300), it initially receives a sensed input signal (Block 302) from the sensing circuit 114. In this embodiment, the processor 112 receives a plurality of samples wherein each of the samples is, preferably, an eight-bit digital representation of the analog signal. The analog signal is comprised of a plurality of samples that have been sampled at a rate of, preferably, either 128 or 256 Hz.

The processor 112 then determines (Block 304) if it is time to compress the data (e.g., based on a request for real-time telemetry data or based on whether the sample signals indicate that a cardiac event meriting storage has occurred). If yes (Block 304), the processor 112 would set a number of initial variables (Block 306). In particular, the processor 112 would set a COUNT variable to zero, a cumulative error variable (CUMERR) to zero, and an initial value for x(n), which is transmitted in an uncompressed format using the first eight-bit digital sample indicative of the actual amplitude of the incoming electrogram signal. As will be described in greater detail below, the COUNT variable and the cumulative error variable assist in the compression of the data. The COUNT variable is the total number of samples that have been approximated as being zero, and the cumulative error variable (CUMERR) is the total error of these approximations.

Thus, for the very first iteration, x(1), will be the initial value obtained (Block 306). However, in subsequent iterations of the compression scheme, the new samples are the delta values between sequentially received samples.

Accordingly, the processor then obtains a new data sample, x(n) (Block 310), which in this embodiment is comprised of an eight-bit digital signal that corresponds to the amplitude of the next sample of the analog electrogram signal.

Next, the processor 112 calculates a DELTA variable (Block 312) in one of two preferred methods. In the first method, the DELTA variable is the difference between the newly obtained sample x(n) and the sample obtained on the previous cycle x(n−1):

$DELTA_n = x(n) - x(n-1)$.

In the second method, the DELTA variable is defined as the PREDICTOR ERROR corresponding to the difference between the newly obtained sample x(n) and a predicted value which is a function of possibly all previous samples x(n−1), x(n−2)−x(0):

$DELTA_n = $ Predictor Error $= x(n) - $ Predicted Value;

wherein the Predicted Value is a function of x(n), x(n−1), ... x(n−M) and 0<M<n.

If the Predictor Value is chosen correctly, more zeros, which are represented in a reduced number of bits, are transmitted, therefore increasing compression. As an example of a predictor, one can use an estimate of the slope from the previous samples to predict the current sample, and will be discussed in more detail below. In either case, the DELTA value requires fewer bits to represent the cardiac signal.

Once the DELTA variable has been calculated, the processor 112 then determines (Block 314) whether the COUNT variable is equal to zero. In this embodiment, the COUNT variable is indicative of the number of successive samples, x(n), where the corresponding DELTA+CUMERR variable is less than a preselected threshold.

In the preferred embodiment, the preselected threshold for the DELTA+CUMERR is an "Error Tolerance Threshold", which is the maximum amount of error before sending a corrected sample.

As will be discussed in greater detail below, compression of the data is partially enhanced by transmitting the count of samples where the change from one sample to the next (i.e., the DELTA+CUMERR variable) is less than the preselected threshold.

In the event that the COUNT variable is equal to zero, the processor 112 then proceeds to (Block 340), where the processor 112 then determines whether the $DELTA_n$ variable is substantially equal to zero (i.e., within an error tolerance).

If the DELTA variable is not equal to zero, the processor 112 then decides (Block 344) whether the DELTA variable is between a second threshold, e.g., within the range defined by the two's complement values of −7 and 6. In the event that the processor 112 determines (Block 344) that the DELTA variable is between the second threshold, then the $DELTA_n$ variable is transmitted (Block 346) in a truncated format (e.g., as a nibble corresponding to a 4-bit binary combination). Subsequently, the processor 112 then returns to obtain the next sample x(n) of the event (Block 310).

Hence, for each succeeding sample, x(n), that has a DELTA variable within the second threshold (e.g., between −7 and 6), a 4-bit nibble can be transmitted that when reconstructed will provide the eight-bit data sample x(n). Hence, for these particular samples x(n), the compression ratio is 2:1.

In the event that the processor 112 determines (Block 344) that the DELTA variable was not within the second threshold, thereby indicating a sudden change in the cardiac signal, then the processor 112 (Block 350) transmits the next predetermined number of bits (e.g., a 4-bit nibble) to be an indicator flag (e.g., a −8 in two's complement notation). The indicator flag indicates that a preselected number of the following bits (e.g., an 8-bit byte) contains the actual amplitude of the DELTA variable, which is transmitted in an uncompressed format (Block 352).

Hence, the processor 112 in this embodiment is programmed to ascertain whether the DELTA variable is within a preselected range that can be transmitted in a 4-bit nibble. In the event that the calculated DELTA value between two succeeding samples is within this preselected range, then it is transmitted as a 4-bit combination. For these samples, a corresponding digital value can be transmitted using half the number of bits as would otherwise be required. However, if the delta value falls outside of the preselected range, a 4-bit nibble is used as an indicator to indicate that the succeeding eight bits define the actual delta value.

As discussed above, another aspect of this particular compression scheme which enhances the compression ratio is that successive DELTA variables having a amplitude that falls within a preselected threshold range (i.e., error tolerance threshold) are simply stored as a COUNT variable which is indicative of the number of succeeding samples for which have DELTA values inside of the threshold range.

The processor 112 in this embodiment is also configured to transmit a COUNT variable in the event that the cumulative error is within a preselected threshold range. In the preferred embodiment, the delta value is corrected by transmitting the sum of CUMERR+DELTA, however one of skill in the art could readily correct for the cumulative error by separately transmitting the CUMERR and the DELTA value, and both methods are within the spirit of the invention.

As will be described in greater detail below, the compression scheme determines whether the DELTA variable is less than a preselected threshold. However, a cumulative error is maintained so that when the DELTA variable corresponding to a particular sample falls outside of the tolerance band, the cumulative error can be added to the DELTA variable so that upon reconstruction the changing portion of the electrogram signal will more accurately reflect the actual amplitude of the signal.

Still referring to FIG. 5A, in the event that the DELTA variable is zero (Block 340), the processor 112 then increments the COUNT variable to 1, the previous cumulative error is added to the DELTA value (Block 343), and then the system returns to Block 310 to obtain the next sample x(n).

Accordingly, the processor 112 determines at Block 314 that the COUNT variable is not equal to zero, and the processor 112 determines (Block 316 of FIG. 5B) whether the DELTA variable plus the cumulative error (CUMERR variable) is within a preselected tolerance.

In the event that the DELTA$_n$ plus CUMERR is within a preselected tolerance range, the processor 112 then proceeds to Block 354, wherein the processor 112 sets the CUMERR variable equal to the previous CUMERR variable plus the DELTA variable. Subsequently, the processor 112 increments the COUNT variable by one (Block 356).

After incrementing the COUNT variable (Block 356), the processor 112 then determines whether the COUNT variable is less than a predetermined maximum value (e.g., 15) (Block 360). The maximum value of the count will depend on the number of bits defining the preferred truncated, or compressed, format. In the preferred embodiment shown in FIGS. 5A and 5B, the compressed format is a 4-bit nibble and the uncompressed format is 8-bit bytes. Using a 4-bit nibble to define the count limits, the absolute amplitude of the 4-bit nibble corresponds to the count of 15. Hence, in Block 360, the processor 112 is determining whether the COUNT has reached the maximum value that can be used for the compressed format.

If the COUNT variable is greater than the predetermined maximum value, then the processor 112 transmits a second indicator flag (Block 362) using a predetermined number of bits (e.g., a 4-bit nibble identifier, corresponding to the number 7 in two's complement notation).

The maximum value of the count will depend on the number of bits defining the truncated, or compressed, format. In the preferred embodiment shown in FIGS. 5A and 5B, the truncated format is a 4-bit nibble and uncompressed is 8-bit bytes. Using a 4-bit nibble to define the count limits, the maximum value of the 4-bit nibble corresponds to a count of 15. Hence, in Block 360, the processor 112 is determining whether a count of 15 has been reached.

Following the second indicator flag, the value of the COUNT is transmitted (Block 363) in the truncated, or compressed, format using the predetermined number of bits (e.g., a 4-bit nibble). Subsequently, the processor 112 resets the COUNT variable as equal to zero (Block 364).

Once the COUNT has been transmitted, then the COUNT is reset to one and the processor 112 returns to Block 310 (FIG. 5A) to obtain the next sample.

In the event that the DELTA$_n$ plus CUMERR is not within a preselected tolerance range ("no" at Block 316), the processor 112 then takes corrective action to compensate for the CUMERR and transmit any COUNT value in the counter.

To achieve this, the processor determines (at Block 318) whether the COUNT is equal to "1". If the COUNT is greater than "1" (indicating that a plurality of samples were at the baseline), then the second indicator flag (e.g., the number 7 in two's complement format) is transmitted (Block 320) to indicate that the count value will follow in the next nibble. Then at Block 324, the actual COUNT will be transmitted. Both the second indicator flag and the actual count are transmitted using the compressed number of bits.

If on the other hand, if the COUNT is equal to "1" (indicating an isolated zero value in the data) a "0" is transmitted (Block 322) using a compressed number of bits.

In either case, the DELTA$_n$ is then set to DELTA$_{n-1}$+ CUMERR, and COUNT and CUMERR are both reset to zero. The processor 112 then decides (Block 344, FIG. 5A) whether the DELTA$_n$ is between the second threshold (e.g., within the range defined by the two's complement values of −7 and 6).

If "yes" at Block 344, then the DELTA$_n$ (i.e., DELTA+ CUMERR) is transmitted (Block 346) in the truncated format (e.g., as a 4-bit nibble).

If "no" at Block 344, thereby indicating a large value for the DELTA+CUMERR, then the processor 112 (Block 350) transmits the first indicator flag (e.g., a −8 in two's complement notation) followed by the actual amplitude of the DELTA variable in an uncompressed format (Block 352).

Hence, this compression scheme uses a 4-bit nibble to store DELTA values that are representative of the change in amplitude of the electrogram signal between one sample and the previous sample provided by the sensor 110. As discussed above, the majority of DELTA values corresponding to the majority of samples can be transmitted as a 4-bit nibble. Hence, for the majority of the eight-bit samples provided by the A/D converter 152 (FIG. 2) only one-half of the bits are being used to encode a digital representation of the samples. Further, a 4-bit count variable can also be used to transmit a signal that is representative of up to 15 samples where the amplitude of the DELTA variable is below a preselected threshold, so that up to 15 consecutive zero values (delta or predictor error values) can be represented in only one byte.

However, it will be appreciated that the threshold range introduces some loss to the signal. Consequently, the threshold range is preferably selected so that the majority of the loss occurs during the period of the electrogram where the signal is not changing significantly (sometimes referred to as the quiescent portion of the signal). Hence, in the more flat-lined portions of an electrogram signal, the signal is stored in a lossy fashion which enhances the compression ratio. In fact, the Applicant has determined that using a sampling rate of 256 samples/sec when the threshold is set to zero, the above-outlined compression scheme has a compression ratio of approximately 2.3:1 using the data sets described above. When the error tolerance is increased to one, the compression ratio increases to 3.3, however, an mean-square error is introduced, which in this case would be 0.192. When the baseline error tolerance is increased to 2, the compression ratio increases to 3.9 and the mean-square error increases to 0.377. Finally, when the baseline error tolerance in this embodiment is increased to 3, the compression ratio is increased to 4.3 with an mean-square error of 0.486. It will be appreciated then that significantly greater amounts of data representative of cardiac events can be stored in the memory 126 when it is compressed in this fashion.

Figure 6:
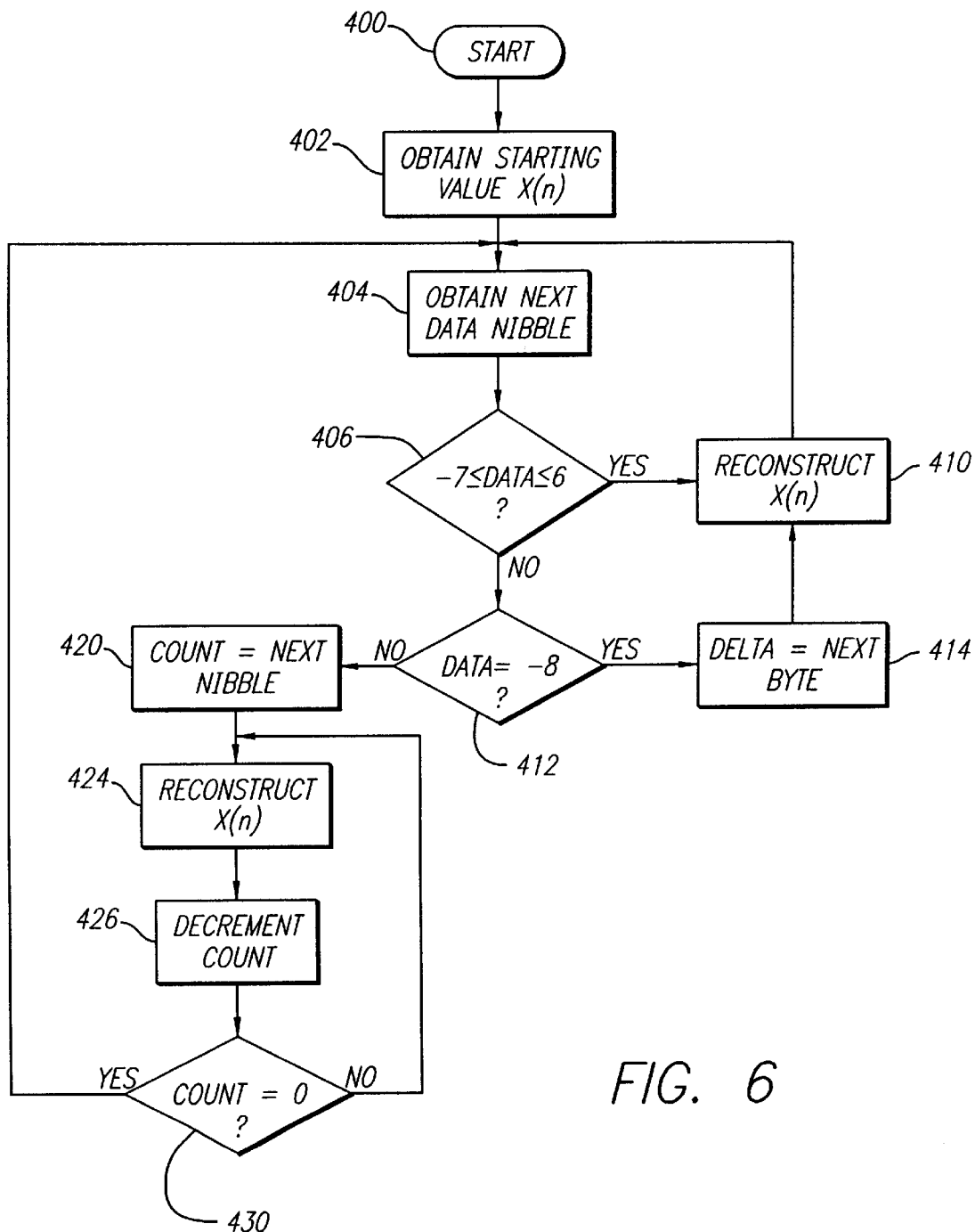
FIG. 6 is an exemplary flow chart illustrating the operation of an external programmer as it reconstructs data, compressed in accordance to the lossy scheme of FIGS. 5A and 5B, that is stored in the memory of the implantable electrical device.

FIG. 6 is a flow chart which illustrates the operation of the external programmer 132 as it reconstructs the electrogram signal from the compressed data that is compressed in accordance with the compression scheme described above in reference to FIGS. 5A and 5B.

In particular, the programmer 132, from a start state (Block 400) proceeds to Block 402 where it obtains the starting value x(n). The starting value is equal to the eight-bit initial value x(n) which is indicative of the amplitude of the electrogram signal being provided. The programmer 132 then reconstructs the electrogram signal using the starting value and the subsequently recorded DELTA values in the manner that will be described below.

In particular, the programmer 132 obtains the next data nibble via the telemetry circuit 130. As discussed above, the data nibble is a 4-bit combination that either stores, in this embodiment, a DELTA value, or provides an indicator that the DELTA value is contained within an eight-bit byte or an indicator that a sequential number of subsequent DELTA values are within a threshold value.

Once the external programmer 132 has obtained the data nibble, the DELTA nibble is then evaluated (Block 406) to determine whether the data nibble is greater than or equal to −7 and less than or equal to 6. In the event the DELTA nibble corresponding to this particular sample x(n) is within this range, then depending on the compression algorithm used, the sample x(n) is either equal to the previous sample x(n−1) plus the encoded data nibble DELTA or the PREDICTOR value (using the previous values of x(n−1), x(n−2) . . . x(M)) and the encoded DELTA nibble.

In the event that the data nibble value is not within this range, then the programmer 132 then determines (Block 412) whether the nibble is an indicator which indicates that the DELTA value is contained within the next eight-bit byte. In this embodiment, the indicator in two's complement notation is −8. In the event that the nibble is the next byte indicator, the external programmer 132 then sets the DELTA variable to the next byte. Hence, the external programmer then determines (Block 410) the sample amplitude as described previously for Block 410. Subsequently, the external programmer 132 returns to Block 404 and obtains the next data nibble.

In the event that the data nibble does not correspond to the indicator for the DELTA variable being stored within the next byte, it must be indicative of the that a plurality of zeros were transmitted. Hence, the external programmer 132 retrieves the next nibble and sets (Block 420) the COUNT variable equal to the next nibble.

In particular, in this embodiment, if the nibble value is not the two's complement equivalent of −8 or −7 through 6, then the nibble value must be the two's complement equivalent of +7 which is an indicator which indicates that the next proceeding nibble corresponds to the count of samples for which the change was less than the threshold value.

The processor determines the reconstructed DELTA variable in one of two methods, corresponding to the two methods described above for compressing the DELTA variable.

In the first method, wherein the DELTA variable was compressed based on x(n)−x(n−1), the processor takes the last known x(n) and effectively adds a zero for each count (Blocks 424, 426 and 430) until the count is zero (yes at Block 430).

In the second method, using the predictor error for the DELTA variable, COUNT indicates the number of samples that were correctly predicted by the prediction algorithm (Block 424). Accordingly, the programmer uses the predictor algorithm to reconstruct COUNT samples.

If the COUNT variable is greater than zero, the external programmer 132 returns to Block 424 where sample x(n) is set equal to the preceding sample x(n−1). This process is repeated for a subsequent number of samples that correspond to the COUNT variable.

From the foregoing, the external programmer 132 reconstructs the samples x(n) by using the initial starting value and then evaluating subsequent 4-bit nibbles to reconstruct the subsequent values. In this embodiment, the 4-bit nibbles define a DELTA variable which is either the difference between two succeeding samples x(n) and x(n−1) or the difference between x(n) and its predicted value. The value of the 4-bit nibble may also be an indicator indicating that there were no changes for a given number of samples, the number of which is contained in the next nibble, or (as in the predictor method) that the difference between x(n) and the predicted value of x(n) is within the error tolerance. Hence, this embodiment of the present invention is capable of compressing electrogram data in a lossy fashion wherein the subsequent data can be reproduced without significant loss of signal.

FIG. 7 is a diagram illustrating various samples that are transmitted using the compression scheme described above in reference to FIGS. 5A, 5B and 6. Specifically, FIG. 7 illustrates that for a given number of DELTA variables wherein the DELTA value of the variable is within a lossy band or less than the preselected threshold, the DELTA variables are transmitted as sequential zeros. Specifically, the first DELTA variable which has a value of zero, is stored as a zero. Subsequently, the next DELTA variable has a value of −1 is also transmitted as a 0. The ninth DELTA variable in this example has a value of −2. However, the cumulative error function of the algorithm would result in the processor 112 transmitting the value of the next DELTA variable as a −3 by adding the value of the previous CUMULATIVE ERROR variable of −1 to the actual DELTA of −2 and transmitting −3.

Hence, FIG. 7 illustrates that large numbers of data signals where the signal is not rapidly changing can be transmitted as sequential zeros using the COUNT and CUMERR variables as described above. This enhances the compression of the algorithm and can, therefore increase the quantity of information that can be transmitted in the same number of bits. It will be further appreciated that the degree of compression can be increased by increasing the lossy band, i.e., increasing the threshold value that the DELTA+ CUMERR value has to change prior to the processor 112 recording a delta value as other than a 0. However, as discussed above, it will be appreciated that increasing the lossy band results in a greater degree of error in the resulting reconstructed signal.

Figure 8A:
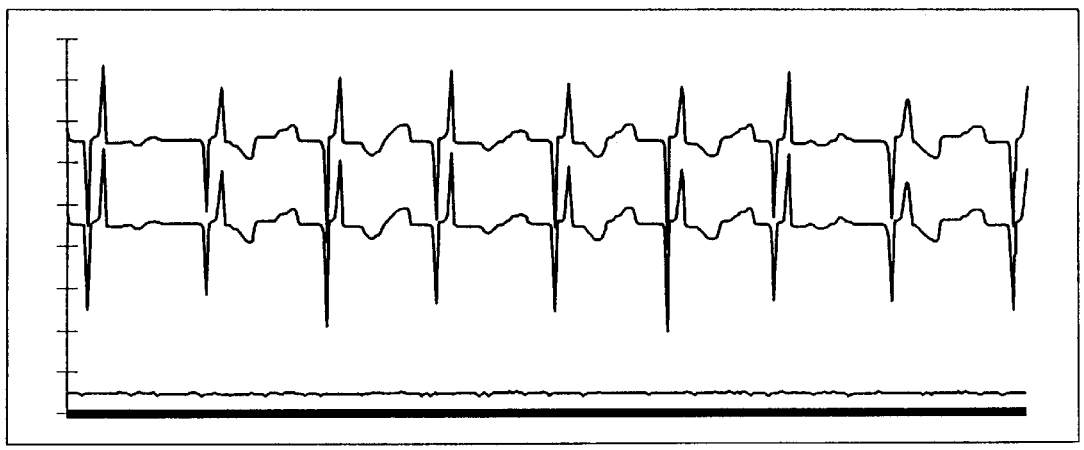
FIGS. 8A–8C are sample electrograms illustrating the original electrogram signal received by the controller of the implantable cardiac device and a corresponding reconstructed signals using the compressed data as lossy compressed by the controller using the compression scheme of FIGS. 5A and 5B, wherein FIGS. 8A–8C correspond to an error tolerance of 1, 2 and 3 about the baseline, respectively.
Figure 8B:
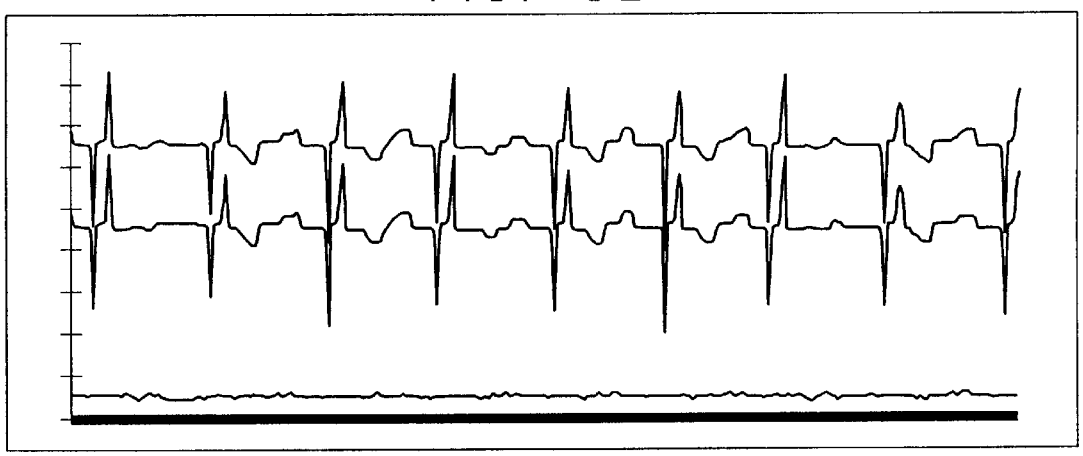
Figure 8C:
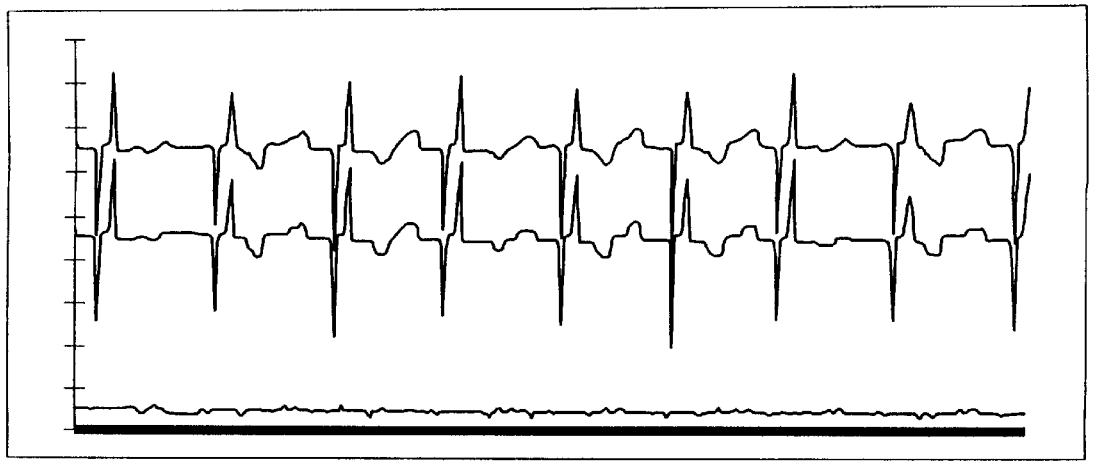

Specifically, FIGS. 8A–8C are exemplary electrogram signals wherein an original electrogram signal is compressed using the compression scheme (upper trace) described above in reference to FIGS. 5A and 5B and reconstructed (lower trace) according to the process described in reference to FIG. 6. In FIG. 8A, the lossy band is set at 1, which means that a DELTA between one sample and a next sample that is 1 or less is transmitted as a 0. As illustrated in FIG. 8A, the reconstructed signal is substantially identical to the originally received electrogram signal. The lowest line on the chart is illustrative of the error between the two signals. However, as shown in FIG. 8B, as the lossy band is increased to a digital 2, the reconstructed signal does not have the same resolution as the reconstructed signal in FIG. 8A and the reconstruction error has been increased. Similarly, when the lossy band is increased to 3 (FIG. 8C), the reconstructed signal is of significantly reduced fidelity and the reconstruction error has increased. Hence, the compression ratio of data that is transmitted can be increased by increasing the lossy band but this increase in memory capacity is achieved at a loss of fidelity in the transmitted signal.

The compression schemes described above have been delta compression schemes wherein the difference between two successive samples are transmitted using a 2-bit or 4-bit compression scheme. In another embodiment, the data that is transmitted in the 2-bit and 4-bit compression schemes described above, can be the difference between the sample received from the sensing circuit 114 and a predictor value.

More specifically, it will be appreciated that various predictor algorithms can be incorporated into the compression scheme. For example, in a first embodiment, a lossy slope estimator is given by:

$$\text{Predicted Value}=x'(n)=2x'(n-1)-x'(n-2) \quad (5)$$

wherein x'(n) is the estimate of x(n), with an error of:

$$\text{err}(n)=x(n)-x'(n). \quad (6)$$

The estimate error, err(n), is used to store data in a compressed fashion. For example, referring back to FIGS. 5A and 5B, the DELTA variable can be set equal to the error value err(n) as calculated above.

In a second embodiment, a lossless slope estimator may be given by:

$$\text{Predicted Value}=x'(n)=2x(n-1)-x(n-2). \quad (5)$$

These equations for the Predicted Value are for illustration purposes. It is recognized that one of skill in the art could readily generate other formulas for the Predicted Value, and these estimates for determining the delta value would all be within the spirit of the invention.

Consequently, the processor 112 upon receiving each new sample, would initially calculate the predicted x'(n) value and then determine the error variable err(n) by calculating the difference between the received sample x(n) and the predictor sample x'(n). This error value can then be transmitted using either the 2-bit or the 4-bit nibble in a manner that is substantially the same as the manner described in conjunction with the delta values calculated above. Specifically, the process would be substantially identical to the process described in FIGS. 3–6 above except that the DELTA variables would instead be equal to a DELTA variable that is the difference between the actual measured value for a particular sample and the predicted value for the sample.

It will be appreciated that any of a number of different predictors can be used to provide data values to be transmitted in a compressed fashion. Hence, the processor 112 can, in one embodiment, be modified to include a predictor which predicts the amplitude of the next sample. Only the difference between the observed sample and the predicted sample would then have to be transmitted. In this embodiment, the external programmer 132 would also be equipped with the same predictor model so that reconstruction of the signal can be achieved.

It will be appreciated that increasingly sophisticated predictor algorithms can be implemented by the processor 112 and the external programmer 132. Specifically, the characteristics of the heart during normal operation and also during cardiac events is somewhat known and predictable. A sophisticated predictor model may be able to recognize the characteristics of a particular heart activity and then predict the next amplitude value with greater accuracy. The more accurate the prediction, the lower the difference or value of the ERR(n) variable that has to be transmitted. Further, the lower the value of the data that is to be transmitted, the fewer the bits that have to be transmitted. Hence, there is a tradeoff between a more sophisticated predictor model and the amount of data that can be transmitted using fewer bits and less memory capacity. Predictors for different arrhythmias can be dynamically selected by the processor for the best compression.

The foregoing embodiments of the present invention have described an implantable cardiac device which incorporates a processor, a memory and a telemetry circuit that is capable of transmitting cardiac event data in a compressed fashion. Advantageously, a signal is transmitted using a decreased number of bits by transmitting a reduced number of bits which are indicative of a change in the sample from either the preceding sample or from a predicted value as opposed to transmitting digital bits representative of the amplitude of the entire sample. The reduced number of bits also have certain values which are indicators of a change which is transmitted in a greater number of bits or is indicative of a successive number of samples wherein the change does not exceed a preselected threshold, e.g., a lossy band.

It will be appreciated that the embodiments of the present invention described herein result in an implantable cardiac device which has enhanced storage capability and can therefore store and transmit greater amounts of data for subsequent downloading to an external programmer. This enhances the ability of doctors and treating physicians to subsequently evaluate cardiac events as more cardiac events can be stored and transmitted to the external device.

Although the foregoing description of the preferred embodiment of the present invention has shown, described and pointed out the fundamental novel features of the invention, it will be understood that various omissions, substitutions and changes in the form of the detail of the apparatus as illustrated, as well as the uses thereof, may be made by those skilled in the art without departing from the spirit of the present invention. Consequently, the scope of the invention should not be limited to the foregoing discussion, but should be defined by the appended claims.

What is claimed is:

1. An implantable cardiac stimulation device having a system for compressing cardiac signals, the stimulation device having a sensing system adapted to sense cardiac signals, a pulse generator configured to generate stimulation pulses in the absence of cardiac signals, and a telemetry circuit that is adapted to transmit the cardiac signals in a compressed format to an external programmer capable of restoring the compressed cardiac signals, the system comprising:

a converter, coupled to the sensing system, configured to convert the sensed cardiac signal to a plurality of digital samples;

a subtractor, coupled to the converter, configured to subtract a current digital sample with a reference value to produce a delta value; and a controller, coupled to the converter, the subtractor and the telemetry circuit, configured to convert the cardiac signal into a compressed format, the compressed format comprising a first digital sample, corresponding to a starting amplitude of the cardiac signal, followed by one of a compressed delta value when the delta value is below a first threshold, or an uncompressed delta value when the delta value is above the first threshold, the uncompressed delta value being preceded by a first indicator signal;

whereby the cardiac signal is compressed in a substantially lossless fashion.

2. The system of claim 1, wherein:

the initial value for the first digital sample comprises a first number of bits;

the compressed delta value comprises a second number of digital bits, the second number of bits being less that the first number of bits; and the uncompressed delta value comprises a third number of digital bits.

3. The system of claim 1, wherein:

the converter converts the cardiac signals into a digital sample having a first number of bits, such that the first digital sample and the uncompressed delta value comprise the first number of bits; and the compressed delta value comprises a truncation of the first number of digital bits.

4. The system of claim 3, wherein:

the compressed delta value comprises a 2-bit combination corresponding to one of a 1-bit change in the positive direction, no change, and a 1-bit change in the negative direction;

the first threshold is greater than a +/−1-bit change in the delta value; and the first indicator signal comprises a unique 2-bit combination.

5. The system of claim 4, further comprising:

a memory, coupled to the controller, that is adapted to store the compressed cardiac signal; and wherein the controller is adapted to trigger the memory to store a count of the number zero values;

whereby the compression of a portion of the cardiac signal in which the delta value is zero uses less memory while being compressed in a substantially lossless fashion.

6. The system of claim 3, wherein:

the compressed delta value comprises a 4-bit combination of bits corresponding the amplitude of the delta value;

the first threshold is defined so as to allow the delta values to be represented in the 4-bit combination; and the first indicator signal comprises a unique 4-bit combination.

7. The system of claim 6, wherein the first threshold is selected so that delta values which fall within a range between a +6 value and −7 value in two's compliment notation are compressed, and delta values which fall outside of the range are uncompressed.

8. The system of claim 6, further comprising:

a memory, coupled to the controller, that is adapted to store the compressed cardiac signal; and wherein the controller is adapted to trigger the memory to store a count of the number of 4-bit combinations that are below a predetermined error threshold and classify such as 'no change';

whereby the compression of a portion of the cardiac signal in which the delta value is below the predetermined error threshold uses less memory while being compressed in a substantially lossy fashion.

9. The system of claim 1, further comprising:

a detector, coupled to the sensing system, configured to detect a predefined cardiac event;

a memory, coupled to the controller, that is adapted to store the compressed cardiac signal; and wherein the controller is coupled to the detector and configured to trigger the storage of the compressed cardiac signals into the memory when the predefined cardiac event is detected.

10. The system of claim 1, wherein:

the telemetry circuit is adapted to receive a request from the external programmer for real-time electrograms; and the controller is coupled to the telemetry circuit and configured to trigger the transmission of the compressed cardiac signals to the telemetry circuit when the real-time electrogram request is received.

11. The system of claim 1, wherein the controller is further configured to monitor the cumulative error up to a predetermined error threshold, and to transmit a corrected delta value when the cumulative error exceeds the predetermined error threshold.

12. The system of claim 1, wherein:

the reference value comprises the previous digital sample, $x(n-1)$; and the DELTA value is determined in accordance with the following equation:

$$\text{DELTA}_n = x(n) - x(n-1).$$

13. The system of claim 1, wherein:

the reference value comprises a predicted value based on two or more of the previous digital samples; and the DELTA value is determined in accordance with the following equation:

$$\text{DELTA}_n = \text{Predictor Error} = x(n) - \text{predicted value}.$$

14. The system of claim 13, wherein:

the reference value is selectable from a plurality predicted values corresponding a plurality of predictors;

the controller is adapted to select an optimum reference value from the plurality of predicted values; and the DELTA value is determined using the optimum reference value.

15. The system of claim 14, further comprising:
a detector, coupled to the sensing system, configured to detect a plurality of cardiac rhythms;
a memory configured to store more than one predicted value based on a plurality of predictors corresponding to a plurality of cardiac rhythms; and
wherein the controller is adapted to select the optimum predicted value for a selected cardiac rhythm to produce a minimum predictor error corresponding to a minimum delta value.

16. An implantable cardiac stimulation device having a system for compressing cardiac signals, the stimulation device having a sensing system adapted to sense cardiac signals, a pulse generator configured to generate stimulation pulses in the absence of cardiac signals, and a telemetry circuit that is adapted to transmit the cardiac signals in a compressed format to an external programmer capable of restoring the compressed cardiac signals, the system comprising:
converting means, coupled to the sensing system, for converting the sensed cardiac signal to a plurality of digital samples, and for producing a first digital sample corresponding to a starting amplitude of the cardiac signal and a plurality of delta values each indicative of a subsequent change in amplitude of the cardiac signal; and
processing means for converting the first digital sample and the plurality of delta values into an encoded string of compressed and uncompressed values, the encoded string comprising the first digital sample in an uncompressed format followed by the plurality of delta values in one of the compressed or uncompressed formats, the processing means for transmitting one of a compressed or uncompressed delta value based on whether a compression criteria has been met, and identifying means for identifying whether the delta value is in one of the compressed or uncompressed formats;
whereby the cardiac signal is compressed in a substantially lossless fashion.

17. The system of claim 16, wherein:
the compressed delta value comprises a 2-bit combination corresponding to one of a 1-bit change in the positive direction, no change, and a 1-bit change in the negative direction; and
the compression criteria comprises a first threshold which is greater than a +/−1-bit change in the delta value;
the identifying means comprises a unique 2-bit combination of bits preceding the uncompressed delta value.

18. The system of claim 17, further comprising:
storing means, coupled to the processing means, that is adapted to store the encoded string; and
wherein the processing means is adapted to trigger the storing means to store a count of the number zero values;
whereby the compression of a portion of the cardiac signal in which the delta value is zero uses less memory while being compressed in a substantially lossless fashion.

19. The system of claim 16, wherein:
the compressed delta value comprises a 4-bit combination of bits corresponding the amplitude of the delta value;
the compression criteria comprises a first threshold which is defined so as to allow the amplitude of the delta values to be represented in the 4-bit combination; and
the identifying means comprises a unique 4-bit combination.

20. The system of claim 19, wherein the first threshold is selected so that delta values which fall within a range between a +6 value and −7 value in two's compliment notation are compressed, and delta values which fall outside of the range are uncompressed.

21. The system of claim 19, further comprising:
storing means, coupled to the processing means, that is adapted to store the encoded string; and
wherein the processing means is adapted to trigger the storing means to store a count of the number of 4-bit combinations that are below the a predetermined error threshold and classify such as 'no change';
whereby the compression of a portion of the cardiac signal in which the delta value is below the predetermined error threshold uses less memory while being compressed in a substantially lossy fashion.

22. The system of claim 21, wherein the processing means comprises means for monitoring the cumulative error whenever the delta value is below the predetermined error threshold, and to transmit a corrected delta value taking into account the cumulative error in response to the monitoring means.

23. The system of claim 16, further comprising:
detecting means, coupled to the sensing system, for detecting a predefined cardiac event;
storing means for storing the encoded string; and
wherein the processing means triggers the storing means to store the encoded string when the predefined cardiac event is detected.

24. The system of claim 16, wherein the processing means comprises means for monitoring the cumulative error up to a predetermined error threshold, and means for transmitting a corrected delta value when the cumulative error exceeds the predetermined error threshold.

25. The system of claim 16, wherein:
the telemetry circuit is adapted to receive a request from the external programmer for real-time electrograms; and
the processing means comprises means for triggering the telemetry circuit to transmit the encoded string to the external programmer when the real-time electrogram request is received.

26. The system of claim 16, further comprising:
subtracting means for subtracting a current digital sample from a reference value and for producing a difference signal thereof; and
wherein the delta value comprises the difference signal.

27. The system of claim 26, wherein:
the reference value comprises a predicted value based on two or more of the previous digital samples; and
the DELTA value is determined in accordance with the following equation:

$$\text{DELTA}_n = \text{Predictor Error} = x(n) - \text{predicted value}.$$

28. The system of claim 26, wherein:
the reference value is selectable from a plurality predicted values corresponding a plurality of predictors;
the processing means includes means for selecting an optimum reference value from the plurality of predicted values; and
the DELTA value is determined using the optimum reference value.

29. The system of claim 28, further comprising:
detecting means, coupled to the sensing system, for detecting a plurality of cardiac rhythms;

means for storing more than one predicted value based on a plurality of predictors corresponding to a plurality of cardiac rhythms; and wherein the processing means includes means for selecting the optimum predicted value for a selected cardiac rhythm to produce a minimum predictor error corresponding to a minimum delta value.

30. The system of claim 26, wherein:

the reference value is the previous digital sample, x(n−1); and the difference signal is determined in accordance with the following formula:

$$\text{DELTA}_n = x(n) - x(n-1).$$

31. A method, for use with an implantable cardiac stimulation device, of compressing a patient's cardiac signal in a compressed format for subsequent reconstruction in an external device, the method comprising the steps of:

converting the cardiac signal into a plurality of digital samples, each digital sample comprising a first number of digital bits;

determining a delta value based on the difference between a reference value and a current digital sample;

determining when the delta value meets a predefined criteria and for producing a first indicator signal when the criteria is not met;

triggering the transmission of an initial first number of bits as a starting value;

triggering the transmission of a compressed digital signal when the predefined compression criteria is met, the compressed digital signal having a second number of digital bits that is less than the first number of digital bits; and triggering the transmission of the first indicator signal followed by the uncompressed delta value when the predefined criteria is not met.

32. The method of claim 31, further comprising the step of:

selecting a previous digital signal for use as the reference value.

33. The method of claim 31, further comprising the step of:

determining a predicted value for use as the reference value.

34. The method of claim 33, further comprising the step of:

determining more than one predicted values for use as the reference value;

determining an optimum predicted value; and determining the DELTA value using the optimum predicted value.

35. The method of claim 31, further comprising the step of:

monitoring the cumulative error up to a predetermined error threshold; and transmitting the corrected delta value when the cumulative error exceeds the predetermined error threshold.

* * * * *